US010665003B2

(12) United States Patent
Polster et al.

(10) Patent No.: US 10,665,003 B2
(45) Date of Patent: May 26, 2020

(54) METHOD FOR CORRECTING A SPATIALLY RESOLVED PHOTON SCAN OF AN X-RAY DETECTOR

(71) Applicant: Siemens Healthcare GmbH, Erlangen (DE)

(72) Inventors: Christoph Polster, Erlangen (DE); Steffen Kappler, Effeltrich (DE); Edgar Goederer, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/202,246

(22) Filed: Nov. 28, 2018

(65) Prior Publication Data
US 2019/0172231 A1 Jun. 6, 2019

(30) Foreign Application Priority Data
Dec. 1, 2017 (DE) .......................... 10 2017 221 728

(51) Int. Cl.
*A61B 6/03* (2006.01)
*G06T 11/00* (2006.01)
*G01T 1/17* (2006.01)
*A61B 6/00* (2006.01)

(52) U.S. Cl.
CPC ............ *G06T 11/008* (2013.01); *A61B 6/032* (2013.01); *A61B 6/4233* (2013.01); *A61B 6/4241* (2013.01); *A61B 6/5205* (2013.01); *A61B 6/5258* (2013.01); *G01T 1/17* (2013.01); *G06T 2207/10081* (2013.01); *G06T 2210/41* (2013.01)

(58) Field of Classification Search
CPC ..... A61B 6/032; A61B 6/4233; A61B 6/4241; A61B 6/5205; A61B 6/5258; G01T 1/17; G06T 11/005; G06T 11/008; G06T 2207/10081; G06T 2210/41
See application file for complete search history.

(56) References Cited

U.S. PATENT DOCUMENTS

2010/0215230 A1* 8/2010 Bornefalk ............. G06T 11/005
  382/128
2011/0116594 A1* 5/2011 Yamakawa ............ A61B 6/032
  378/19

(Continued)

OTHER PUBLICATIONS

German Office Action for Application No. DE20107221728.6 dated Jul. 25, 2018.

(Continued)

*Primary Examiner* — Mark R Gaworecki
(74) *Attorney, Agent, or Firm* — Harness, Dickey & Pierce, P.L.C.

(57) ABSTRACT

A method and an X-ray detector are for correcting a spatially resolved photon scan of the X-ray detector. In an embodiment, the X-ray detector includes processing circuitry configured to: generate, from an incident X-ray photon, a signal contribution in a first electrical signal in a spatially resolved manner, a reference value being defined by an absence of X-ray photons; resolve, in relation to the reference value, positive signal contributions of the first electrical signal and negative signal contributions of the first electrical signal; and provide the positive signal contributions resolved and the negative signal contributions resolved for further processing.

27 Claims, 7 Drawing Sheets

(56) References Cited

U.S. PATENT DOCUMENTS

| | | | | |
|---|---|---|---|---|
| 2011/0121191 A1* | 5/2011 | Kappler | .................... | G01T 1/17 |
| | | | | 250/370.09 |
| 2011/0311022 A1* | 12/2011 | Kappler | .................. | G01T 1/247 |
| | | | | 378/19 |
| 2013/0168562 A1 | 7/2013 | Brambilla et al. | | |
| 2015/0374317 A1* | 12/2015 | Moriyasu | ............. | A61B 6/4241 |
| | | | | 378/5 |

OTHER PUBLICATIONS

Taguchi, Katsuyuki et al. "Vision 20/20: Single photon counting x-ray detectors in medical imaging" Medical Physics, vol. 40, No. 10, 2013; PMID: 24089889, PMCID: PMC3786515, DOI: 10.1118/1.4820371; 2013.

* cited by examiner

METHOD FOR CORRECTING A SPATIALLY RESOLVED PHOTON SCAN OF AN X-RAY DETECTOR

PRIORITY STATEMENT

The present application hereby claims priority under 35 U.S.C. § 119 to German patent application number DE 10 2017 221 728.6 filed Dec. 1, 2017, the entire contents of which are hereby incorporated herein by reference.

FIELD

Embodiments of the invention generally relate to a method for correcting a spatially resolved photon scan of an X-ray detector, wherein in the X-ray detector, from an incident X-ray photon, a signal contribution is generated in a first electrical signal in a spatially resolved manner, wherein for the first electrical signal an upper threshold value is selected wherein the first electrical signal is compared in a spatially resolved manner with the upper threshold value and if the upper threshold value is exceeded, a signal contribution of a second electrical signal is generated spatially resolved in each case and wherein on the basis of the second electrical signal, an image data set is generated.

BACKGROUND

In a computed tomography (CT) system, an X-ray image is generated from the body of a patient to be examined from different polar angle directions relative to his body axis in each case and subsequently, from the individual X-ray images which each represent the absorption of the X-rays by the body tissue for the respective angle directions, a three-dimensional volumetric model of the body tissue is reconstructed. The spatial resolution of this volumetric model depends, firstly, on the spatial resolution of the individual X-ray images, that is, on the resolving power of the X-ray detector and, secondly, on the absorption contrast, i.e. in how much detail the varying absorption of the X-ray radiation that is irradiated from the relevant angle onto the body tissue can be represented in a single X-ray image. In order herein always to be able to keep the radiation dose for the patient under examination to a medically acceptable level, X-ray detection which is also still able, for a relatively low radiation dose in a single X-ray image, to represent the different absorption by different tissue layers with sufficient contrast is advantageous.

Both for the greatest possible spatial resolution as well as for the most contrast-rich representation possible of different absorption levels with simultaneously moderate X-ray radiation, quantum-counting X-ray detectors have proved to be advantageous. In a quantum-counting X-ray detector, an incident X-ray photon initially generates a free electron in a semiconductor, for example cadmium telluride, by ionization of one of the lattice atoms which, as a consequence of its remaining kinetic residual energy, in turn ionizes further lattice atoms, so that an electron-hole-pair cloud forms in the semiconductor. The electrons or holes are now each collected by pixelated anodes or cathodes to each of which a bias voltage is applied. On arrival of an electron cloud at an anode pixel, therefore, a current pulse and from this, via a pre-processing, usually a voltage pulse is generated from which the relevant X-ray photon which was responsible for the generation of the electron cloud in the region of the anode pixel can be inferred.

Due to the effects of mirror charges, however, an X-ray photon especially in the boundary region of two detector pixels can lead, through induction to a current pulse or a voltage pulse in the adjacent pixel, i.e. by way of its charge cloud, the X-ray photon generates a corresponding voltage pulse in the detector pixel at the location of its arrival and, in the region of the adjacent pixel, as a result of the charges induced there, a further usually weaker, voltage pulse. This can lead, as a consequence of the counting events which are evoked only though induction from an adjacent region and not through a separate X-ray photon itself, to a worsening of the image contrast. Particularly in the case of a high spatial resolution which is actually desirable for computed tomography, this can become a problem especially due to the edge region being enlarged relative to the overall area of a pixel, in which edge region such induced charges can occur.

Quantum-counting detectors allow a particular minimum energy to be set below which X-ray photons cannot be detected at all. In order to filter the induction-based counting events, that is voltage pulses, which have actually been created by an X-ray photon in an adjacent pixel, the minimum energy can be increased far enough that the induction-based voltage pulses which are weaker than the voltage pulses of the "correct" counting events are no longer registered. This, however, has the disadvantage that also per se "correct" voltage pulses with correspondingly low energy of the causative X-ray photon are no longer detected, which again worsens the image contrast.

SUMMARY

At least one embodiment of the invention generally relates to, in a spatially resolved photon scan, correcting such counting events which arise in a detector pixel not by way of an arriving X-ray photon, but only by way of an induction from an adjacent pixel. At least one embodiment of the invention further relates to an X-ray detector with which the correction of such counting events is possible.

At least one embodiment of the invention is directed to a method for correcting a spatially resolved photon scan of an X-ray detector, wherein in the X-ray detector, a signal contribution from an incident X-ray photon is generated in a first electrical signal in a spatially resolved manner, wherein a reference value for the first electrical signal is defined by an absence of X-ray photons, wherein for the first electrical signal in each case an upper threshold value above the reference value and a lower threshold value below the reference value are selected, wherein the first electrical signal is compared in a spatially resolved manner with the upper threshold value and if the upper threshold value is exceeded, a signal contribution of a second electrical signal is generated spatially resolved in each case, wherein the first electrical signal is compared in a spatially resolved manner with a lower threshold value and if the lower threshold value is undershot, a signal contribution of an electrical correction signal is generated in a spatially resolved manner and wherein the second electrical signal is corrected by the correction signal, and on the basis of the corrected second electrical signal, an image data set is generated.

At least one embodiment of the invention is directed to a method for correcting a spatially resolved photon scan of an X-ray detector, comprising:

generating in the X-ray detector, from an incident X-ray photon, a signal contribution in a first electrical signal in a spatially resolved manner, wherein a reference value for the first electrical signal is defined by an absence of X-ray photons;

selecting, for the first electrical signal, an upper threshold value above the reference value and selecting a lower threshold value below the reference value;

first comparing the first electrical signal in a spatially resolved manner with the upper threshold value;

generating, upon the first comparing indicating that the upper threshold value is exceeded, a signal contribution of a second electrical signal, spatially resolved;

second comparing the first electrical signal, in a spatially resolved manner with the lower threshold value;

generating, upon the second comparing indicating that the lower threshold value is undershot, a signal contribution of a correction signal;

correcting the second electrical signal based upon the correction signal; and generating, based upon the second electrical signal corrected, an image data set.

At least one embodiment of the invention is directed to an X-ray detector for the spatially resolved detection of X-ray photons and which is configured to generate, from an incident X-ray photon, a signal contribution in a first electrical signal in a spatially resolved manner, for which a reference value is defined through an absence of X-ray photons, and to resolve, both in relation to the reference value, positive signal contributions and also in relation to the reference value, negative signal contributions of the first electrical signal and to provide them for further processing. The advantages given for embodiments of the method and for its developments can be transferred analogously to the X-ray detector.

At least one embodiment of the invention is directed to an X-ray detector for spatially resolved detection of X-ray photons, the X-ray detector comprising:

processing circuitry configured to:

generate, from an incident X-ray photon, a signal contribution in a first electrical signal in a spatially resolved manner, a reference value being defined by an absence of X-ray photons; and resolve, in relation to the reference value, positive signal contributions of the first electrical signal and negative signal contributions of the first electrical signal; and providing the positive signal contributions resolved and the negative signal contributions resolved for further processing.

At least one embodiment of the invention further concerns an imaging medical device comprising an X-ray source for generating X-ray photons and an X-ray detector of at least one embodiment, configured for carrying out at least one embodiment the method described. The advantages cited for embodiments of the method and its developments and for embodiments of the X-ray detector and its developments can be transferred analogously to the imaging medical device.

BRIEF DESCRIPTION OF THE DRAWINGS

An example embodiment of the invention will now be described in greater detail making reference to the drawings. In the drawings, in each case, shown schematically.

Figure 1:
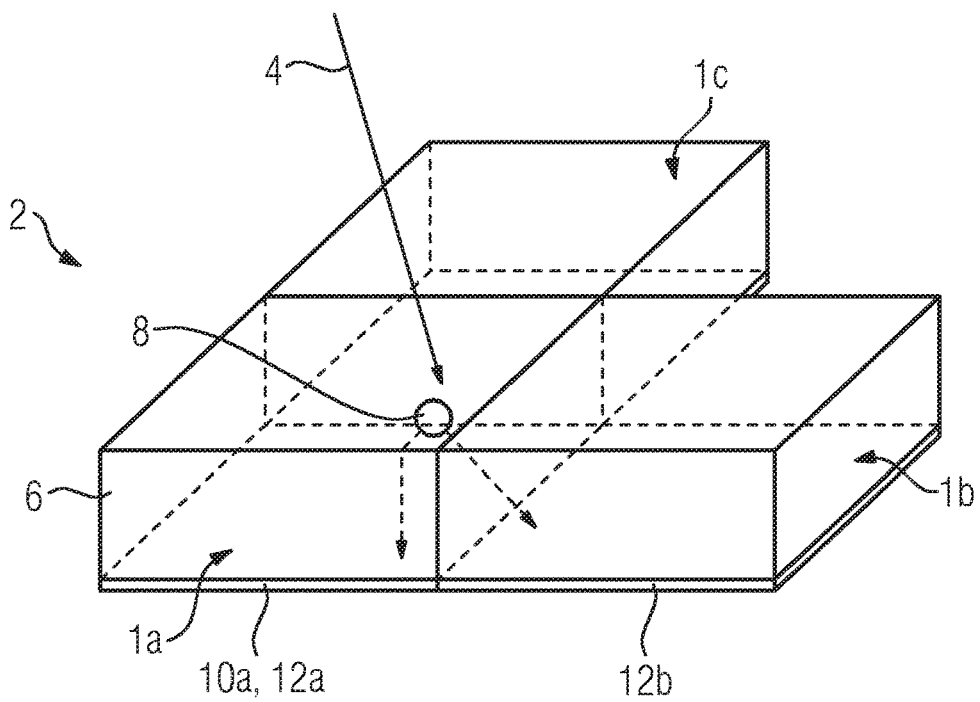
FIG. 1 is an oblique view of an X-ray photon incident upon the detector pixels of an X-ray detector.

Parts and variables which correspond to one another are provided with the same reference signs in all the drawings.

DETAILED DESCRIPTION OF EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention is directed to a method for correcting a spatially resolved photon scan of an X-ray detector, wherein in the X-ray detector, a signal contribution from an incident X-ray photon is generated in a first electrical signal in a spatially resolved manner, wherein a reference value for the first electrical signal is defined by an absence of X-ray photons, wherein for the first electrical signal in each case an upper threshold value above the reference value and a lower threshold value below the reference value are selected, wherein the first electrical signal is compared in a spatially resolved manner with the upper threshold value and if the upper threshold value is exceeded, a signal contribution of a second electrical signal is generated spatially resolved in each case, wherein the first electrical signal is compared in a spatially resolved manner with a lower threshold value and if the lower threshold value is undershot, a signal contribution of an electrical correction signal is generated in a spatially resolved manner and wherein the second electrical signal is corrected by the correction signal, and on the basis of the corrected second electrical signal, an image data set is generated.

Advantageous, and partly per se inventive, embodiments are the subject matter of the subclaims and the description below.

The concept of a first electrical signal covers, in particular, a voltage signal and a current signal. A signal contribution in the first electrical signal should be understood herein, in particular, to be a deviation of the signal value from the reference value. A definition of the reference value by an absence of X-ray photons should herein be understood, in particular, in that the reference value is given by the value of the first electrical signal which the first electrical signal takes in a total absence of X-ray photons, as can be achieved, for example, by way of a corresponding absolutely photon-impervious blocking in the relevant spectral region of the X-ray detector. A spatially resolved generation of a signal carry-over in the first electrical signal by the incident X-ray photon should be understood, in particular, as meaning that on the basis of the signal contribution and the corresponding information contained therein, the location of the incidence on the X-ray detector can be determined at least approximately, wherein as possible incidence locations, in particular, a plurality of positions on the X-ray detector are available.

In particular, the upper threshold value and/or the lower threshold value for the first electrical signal can each be selected location-dependently, that is, that for the different signal contributions, in the context of the spatial resolution of their creation, different values for the upper or the lower threshold value can be selected. In particular, however, the upper and/or lower threshold value for all the possible signal contributions in the first electrical signal in the context of the spatial resolution can also be selected to be identical. The signal contribution that is generated in the X-ray detector from the incident X-ray photon spatially resolved in the first electrical signal contains, in particular, an item of information regarding the energy of the generating X-ray photon and particularly preferably permits a proportionality to the energy to be produced, for example, on the basis of a pulse height of a signal pulse as a signal contribution or on the basis of a time integral over such a pulse height.

The spatially resolved generation of a signal contribution in the second electrical signal on exceeding the upper threshold value by a corresponding signal contribution in the first electrical signal can take place, in particular, in that only those values of the first signal which exceed the upper threshold value are used. On exceeding the upper threshold value by a signal contribution in the first signal, a natural number, preferably 1, can now be generated in the second signal as the value of the generated signal contribution. Preferably, on undershooting the lower threshold value by the corresponding signal contribution of the first electrical signal as a signal contribution of the electrical correction signal, a value, preferably 1, which is constant for all possible signal contributions of the first electrical signal is generated. In this case, the X-ray detector operates as a quantum-counting detector.

Signal contributions which are generated in a spatially resolving X-ray detector by an X-ray photon which is incident upon a particular detector pixel usually supply, by reason of the direct charge flow in the relevant detector pixel, a unipolar signal pulse that, with suitable normalization is positive, in a corresponding current signal. If the current signal is converted into a voltage signal for better processing, then it is possible also to generate from the unipolar signal pulse in the current signal, an unpolarized signal pulse in the voltage signal. In order now to generate a corresponding counting event from such a signal pulse and herein to keep the signal contrast as high as possible in relation to possible noise, the upper threshold value is selected so that counting events which do not correspond to an X-ray photon incident upon the detector pixel can be prevented. This applies, in particular, for signal pulses which are not generated by a photon incident on the relevant detector pixel itself, but by a photon which is incident on the adjacent detector pixel and thereby causes an induction of charge carriers.

The relevant signal pulses of such induction-based signal contributions, that is, those that are created by X-ray photons which are incident upon adjacent detector pixels, however, are initially bipolar in the current signal as a result of the changing charge flow of the induction to the charge equalization. This means that in the context of the corresponding normalization, they have at first a positive pulse shape with a subsequent backswing to a minimum beneath the value representing an absence of the X-ray photons, in order subsequently to return to this value again. Accordingly, a voltage pulse with a bipolar pattern can also be generated from a bipolar current pulse of this type. This can take place, for example, via a current-voltage converter, for instance in the form of a transimpedance amplifier.

Depending on the choice of current signal or voltage signal as the first electrical signal, the signal pulse therefore has a minimum lying below the reference value in order to return subsequently to the reference value. According to the method, such signal pulses are now removed from the counting—since they objectively correspond to no X-ray photon incident upon the detector pixel—in that the underswing now creates a signal contribution in the correction signal with its pulse minimum. By this, the corresponding counting events based on induction rather than on a real incident X-ray photon in the second electrical signal can be corrected by simple devices/methods.

Preferably herein the second electrical signal is corrected through a simple subtraction from the corresponding spatially resolved signal contributions by the correction signal.

Suitably, the signal contribution of the first electrical signal is generated in a quantum-counting manner. For a quantum-counting X-ray detector, the method given is particularly advantageous since herein simple counting events can be counted up against one another.

Preferably, the ratio is selected from the amount of the lower threshold value and the amount of the upper threshold value, each related to the reference value, between 0.3 and 3, particularly preferably between 0.5 and 2. This means that the difference amount between the upper threshold value and the reference value on one side and the difference amount between the lower threshold value and the reference value on the other side have a ratio to one another which falls within the value interval given. By this, it can be ensured firstly that the corresponding underswings are correctly registered and lead to corresponding signal contributions in the correction signal and secondly the upper threshold value can be kept sufficiently low, so that low-energy X-ray photons can also be detected. This leads to an advantageous signal contrast since, as a result of the higher absorption level of low-energy X-ray photons in the body tissue, the items of information on the transmission of these X-ray photons are particularly valuable.

Favorably, the lower threshold value is selected to be in an interval from 5 keV to 15 keV, particularly preferably between 5 keV and 10 keV below the reference value. This means that the energy of an incident X-ray photon is taken into account by the respective normalization of the first electrical signal such that on the basis of the first electrical signal, the energy of the creating X-ray photon can be recognized. The lower threshold value is then selected so that the energy of an X-ray photon corresponding to the threshold value lies within the stated interval. By this, firstly, signal contributions in the correction signal due to electronic noise in the first electrical signal can be prevented and, secondly, it can be achieved that as many underswings of bipolar signal pulses as possible are detected, which leads to a correction of particularly many induction-based and not "X-ray photon-generated" signal contributions in the individual detector pixels.

It has further proved to be advantageous if the second electrical signal is locally corrected by the correction signal in a pixel electronics unit of the X-ray detector, and from this a third electrical signal is generated, wherein the image data set is generated on the basis of the third electrical signal. This means, in particular, that the second electrical signal is corrected, in the totality of its signal contributions with the relevant spatial information regarding the corresponding generating locations of the first electrical signal in the X-ray detector, by the correction signal, in the totality of its signal contributions with the corresponding spatial information regarding the undershoots of the lower threshold value by the first electrical signal, signal contribution by signal contribution, directly locally in the pixel electronics unit. A pixel electronics unit herein covers, in particular, electrodes for collecting charge carriers and for the corresponding generation of a current signal.

In at least one embodiment, a X-ray detector is configured to correct the relevant signal contributions in the second electrical signal and in the correction signal directly in the individual detector pixels and also before a further processing, as takes place, for example, in an application-specific integrated circuit (ASIC) connected to the pixel electronics unit, and to generate the third electrical signal which is then further processed accordingly in the respective ASICs which are connected to the individual pixel electronics units, for example, by way of a corresponding signal amplification. A local and, in particular pixel-wise generation of the third electrical signal has the advantage herein that only the latter must still be further processed, which saves power and computational resources.

The correction can herein take place, for example, in that the upper and lower threshold values are each selected to be only large enough so that an undesirable quantum noise can still just be suppressed and beyond this all signal contributions in the first electrical signal lead to corresponding signal contributions in the second electrical signal or in the correction signal. Then, for a correction and thus a generation of the third electrical signal, in a preferred embodiment, positive current pulses of the second electrical signal are simply offset with negative current pulses of the correction signal. Based upon the third electrical signal resulting therefrom, the actual counting events can then be determined.

In an advantageous embodiment of the invention, the second electrical signal and the correction signal are each transferred by a pixel electronics unit of the X-ray detector to an ASIC, wherein the second electrical signal is locally corrected in the ASIC by the correction signal, and from this a third electrical signal is generated, and wherein the image data set is generated on the basis of the third electrical signal. By way of the correction of the second electrical signal outside the actual pixels of the X-ray detector, it can be achieved that in the event of a problem or a defect in the circuit for implementing the correction, the sensitive components of the X-ray detector responsible for generating the first electrical signal are not affected by measures to remedy the defect. In that the correction also takes place in the ASIC which is typically connected directly to a pixel electronics unit, the correction still takes place sufficiently locally in order to require only a signal feed of the third electrical signal for the further processing.

Suitably, the second electrical signal and the correction signal are each transferred by an ASIC to a central signal processing unit, wherein the second electrical signal is corrected in the central signal processing unit by the correction signal, and from this a third electrical signal is generated, wherein the image data set is generated on the basis of the third electrical signal. This includes, in particular, that the second electrical signal is transferred in the totality of its signal contributions with the relevant spatial information regarding the corresponding generating locations of the first electrical signal in the X-ray detector by the individual ASICs, each of which are assigned to one or a small group of detector pixels, initially signal contribution by signal contribution to the central signal processing unit, and the correction by the correction signal takes place in the totality of its signal contributions with the corresponding spatial information regarding the undershoots of the lower threshold value by the first electrical signal, in the central signal processing unit.

The correction in a central signal processing unit beyond the ASIC has the advantage that the individual ASICs must only be configured for a minimum of functions necessary for signal processing and amplification and do not additionally need to be conceived and provided with power for the correction.

Preferably, the second electrical signal and the correction signal are each transferred by a central signal processing unit on a rotating portion of a CT system to a fixed portion of the CT system, wherein the second electrical signal is corrected by the correction signal on the fixed portion of the CT system, and from this a third electrical signal is generated, wherein the image data set is generated on the basis of the third electrical signal. The correction of the second electrical signal on the fixed portion of the CT system has the advantage that thereby no additional power must be transferred to the rotating portion for the logical operations which implement the correction to the second electrical signal.

In an advantageous embodiment of the invention, the second electrical signal and the correction signal are each transferred to an image processing unit, wherein from the second electrical signal a data set of preliminary images is created, wherein from the correction signal a correction image data set is generated and wherein the image data set is generated from the data set of preliminary image data and the correction image data set. This comprises, in particular, that the X-ray detector is arranged on the rotating portion of a CT system and the image processing unit is arranged on the fixed portion of a CT system. The creation of the image data set on the basis of a data set of preliminary image data generated from the second electrical signal and of a correction image data set generated from the correction signal has the advantage that for this the infrastructure of the image processing unit already present for a generation of image data can be used to minimize the influences of the counting events represented in the signal contributions of the correction signal on the final image data set.

The actual embodiment of the correction of the second electrical signal and/or the generation of the image data set can herein be selected dependent upon further requirements which can result, in particular, from the X-ray detector itself that is to be used and/or from the higher-level application, for example, a CT system.

At least one embodiment of the invention is directed to an X-ray detector for the spatially resolved detection of X-ray photons and which is configured to generate, from an incident X-ray photon, a signal contribution in a first electrical signal in a spatially resolved manner, for which a reference value is defined through an absence of X-ray photons, and to resolve, both in relation to the reference value, positive signal contributions and also in relation to the reference value, negative signal contributions of the first electrical signal and to provide them for further processing. The advantages given for embodiments of the method and for its developments can be transferred analogously to the X-ray detector.

In a further advantageous embodiment, the X-ray detector comprises a converting detector material for generating charge carriers from an incident X-ray photon, a spatially resolving electrode arrangement and a plurality of current-voltage converters. Herein, the X-ray detector is further configured, in order to generate a spatially resolved signal contribution in the first electrical signal from the charge carriers generated through an incident X-ray photon spatially resolved by way of the electrode arrangement, to generate a current pulse and on the basis of the current pulse by way of one of the current-voltage converters to generate a voltage pulse as a signal contribution in the first electrical signal.

Preferably, the converting detector material is herein provided by a semiconductor or a suitably configured ceramic material. In particular, the electrode arrangement is in direct contact with the converting detector material and is also configured, by way of a voltage applied to the electrode arrangement, to collect the charge carriers generated in the detector material by an incident X-ray photon and thereby to generate the current pulse. According to the voltage to be applied and the charge carriers thereby to be collected, this is a cathode or anode arrangement. The selection of the charge carriers to be collected and correspondingly of the voltage to be applied is preferably made dependent upon the charge carrier mobility in the converting detector material.

For spatial resolution, the electrode arrangement is preferably subdivided into individual electrode pixels so that each individual current-voltage converter is connected to a small number, particularly preferably to exactly one electrode pixel. The current-voltage converter concerned then receives a current pulse generated in the corresponding electrode pixel from the collected charge carriers and converts it into a voltage pulse which is further processed in the prescribed manner as a signal contribution in the first electrical signal.

Favorably, the current-voltage converters are herein each configured, on the basis of a unipolar current pulse generated by an incident X-ray photon, to generate a voltage pulse and, on the basis of a bipolar current pulse, to generate a bipolar voltage pulse. Preferably, the current-voltage converter is herein operated such that between current pulses which are generated by X-ray photons of different energies and the resultant voltage pulses, there is a monotonic relationship. I.e. on the basis of a maximum pulse amplitude of the resultant voltage pulse or a time integral over the voltage pulse, a conclusion can be drawn regarding the energy of the incident X-ray photon. This is particularly advantageous for the further processing, in particular with regard to the correction of the induction-based counting events. An additional advantage of such voltage pulses lies in that as a result of the monotonicity, the relevant voltage steps can be implemented only via comparators.

In the actual implementation of the current-voltage converter, care should always be taken that the conversion reacts sufficiently rapidly to changes in the current pulse so that the different contributions of bipolar current pulses which are generated from induced charges are not "integrated" during the conversion process to a unipolar voltage pulse. On the other hand, in the conversion of a unipolar current pulse, self-excited oscillations in the voltage pulse that can arise from too low a phase reserve of the current-voltage converter must be prevented. For this purpose, firstly the current-voltage converter can be largely operated with a linear characteristic and subsequently a corresponding filter which has been adapted in its transfer function to the stated requirements can be connected downstream of the current-voltage converter, for example with passive RC members. The current-voltage converter can, however, also be adjusted with regard to its own transfer function to these requirements, for example, by way of a corresponding selection of a feedback impedance in the converter or similar.

Suitably, the current-voltage converters are each integrated into an application-specific integrated circuit (ASIC), each of which comprises an amplifier stage. Preferably, the individual current-voltage converters are themselves each formed by an amplifier stage, e.g. in the form of a transimpedance amplifier. The embodiment of the current-voltage converter as an amplifier stage has the advantage that firstly the current pulses generated have a relatively low signal amplitude for the typical signal processing unit, whereas the conversion into a voltage pulse can be accompanied by an amplification of the signal amplitude. Secondly, the pulse form of the voltage pulses generated from the current pulses can be controlled particularly easily via a transfer function of the amplifier stage or via a filter connected downstream of the amplifier stage. The integration of the current-voltage converter into an ASIC has the additional advantage that the circuit can be optimized specifically for the generation of voltage pulses with the aforementioned properties.

At least one embodiment of the invention further concerns an imaging medical device comprising an X-ray source for generating X-ray photons and an X-ray detector of at least one embodiment, configured for carrying out at least one embodiment the method described. The advantages cited for embodiments of the method and its developments and for embodiments of the X-ray detector and its developments can be transferred analogously to the imaging medical device.

Preferably, the imaging medical device is configured as a computed tomography system. In view of the high demands placed on the image quality and in particular on the contrast of the individual recordings that are used in a computed tomography system for generating the volumetric model of the tissue to be investigated, the use of at least one embodiment of the method described in conjunction with at least one embodiment of the X-ray detector described is particularly advantageous.

Favorably, the imaging medical device is configured as a C-arm device. For devices of this type and the demands placed on image quality therein, the method described and the X-ray detector described also prove to be particularly advantageous.

Shown schematically in FIG. 1 in an oblique view are detector pixels 1a, 1b, 1c of a quantum-counting X-ray detector 2. An X-ray photon 4 incident in the region of the pixel 1a initially generates a charge cloud 8 by ionization in a semiconductor crystal 6. The charge cloud 8 now diffuses as a result of a correspondingly applied bias voltage in the region of the detector pixel 1a toward the pixel electronics unit 12a which comprises a suitable anode 10a. In the pixel electronics unit 12a, the charge cloud 8 that is evoked by the X-ray photon 4 generates a current pulse which is processed in an ASIC (not shown in detail) to a voltage pulse. As a consequence of induction, however, in the pixel electronics unit 12b which is assigned to the detector pixel 1b, a corresponding current pulse is also generated which is processed to a voltage pulse. These voltage pulses are each shown in FIG. 2.

Figure 2:
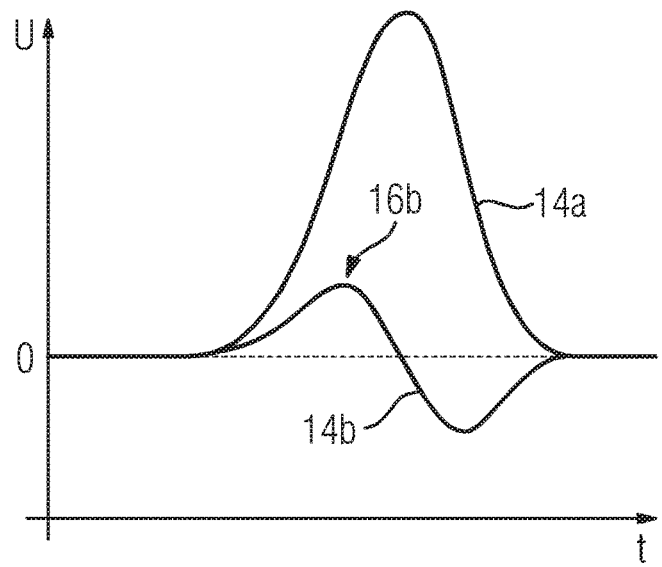
FIG. 2 is a graphical representation of voltage pulses generated by an X-ray photon in the detector pixels according to FIG. 1.

In FIG. 2, the voltage pulses 14a, 14b which have been acquired on the basis of the current pulses generated in the detector pixels 1a, 1b according to FIG. 1 are plotted on a graph against time t. For the voltage pulse 14a, the voltage U is proportional to the energy of the incident X-ray photon. In the present case, the respective current pulse was processed via a suitable current-voltage converter such that the unipolar positive current pulse which the X-ray photon 4 generates in the detector pixel 1a creates the unipolar voltage pulse 14a, whereas the bipolar current pulse which the X-ray photon 4 generates in the detector pixel 1b, generates the bipolar voltage pulse 14b.

It is clearly apparent that the peak of the voltage pulse 14b lies less than an order of magnitude below the peak of the voltage pulse 14a. If the voltage pulse 14a originates from a particularly highly energetic X-ray photon and if the location of the incidence in the pixel 1a is particularly near to the edge with the adjacent pixel 1b, then the peak 16b of the voltage pulse 14b can certainly lie in an order of magnitude in which independent counting events of X-ray photons of lower energy can also lie. In order to prevent the voltage pulse 14b leading to a corresponding counting event which provides a contribution to the X-ray image, a correction that is described by reference to FIG. 3 is applied.

Figure 3:
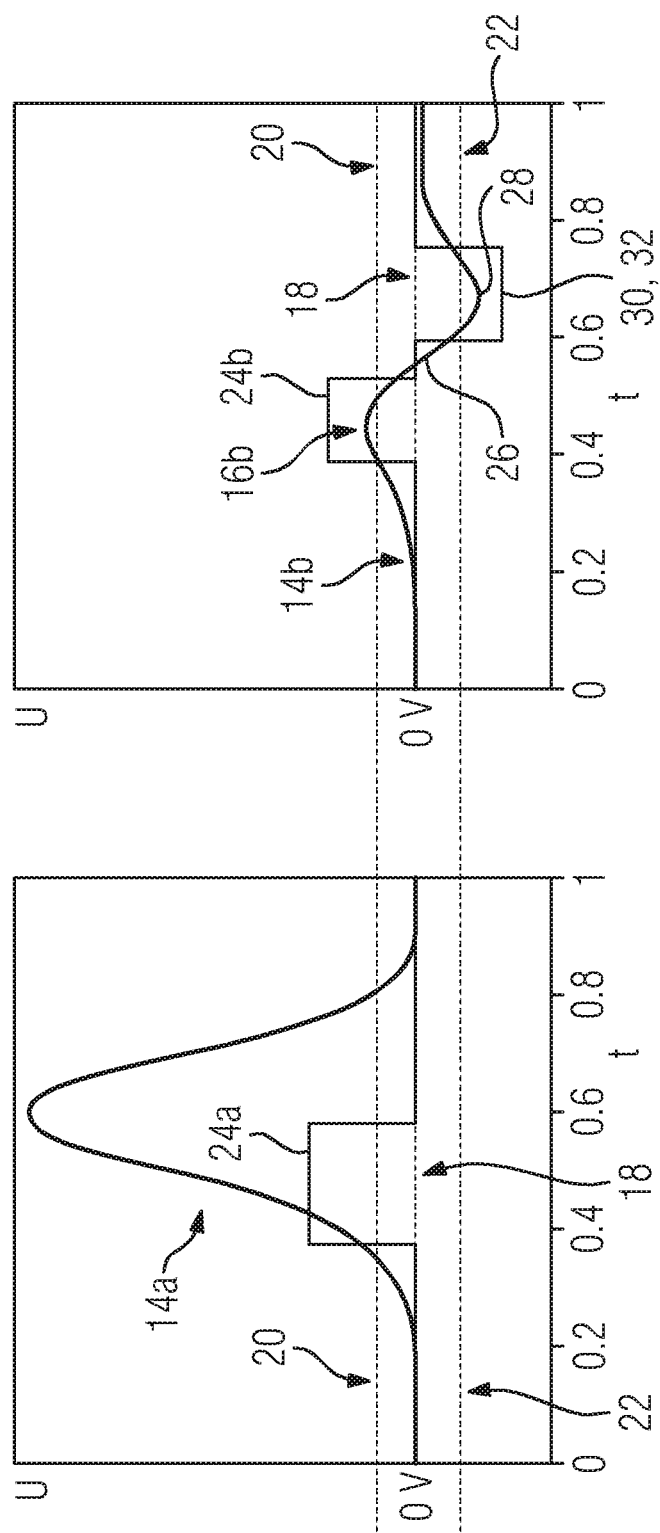
FIG. 3 is a representation and corresponding correction of counting events in the voltage pulses according to FIG. 2.

In FIG. 3, the voltage pulse 14a and the voltage pulse 14b according to FIG. 2 are plotted against time t in separate graphs for greater clarity. The time range shown corresponds to the minimum time resolution of the X-ray detector. The voltage value of 0V is selected so that in a corresponding signal, this value is present in the absence of X-ray photons. The value of 0V applies from now on as the reference value 18. However, this is only one possible selection for a reference value. The reference value can also be selected, for example, by a corresponding linear scaling of a voltage region between the supply voltage and the chassis of a transimpedance amplifier generating the first electrical signal, wherein the value of 0V is assigned to the chassis.

Now an upper threshold value 20 and a lower threshold value 22 are selected consistently for both voltage pulses 14a, 14b. Preferably, the upper threshold value 20 and the lower threshold value 22 are each selected to be the same for all the detector pixels of a detector. This simplifies the correction since, as a consequence of the consistency across the detector, additional assumptions can be dispensed with. As a consequence of the exceeding of the upper threshold value 20 by the voltage pulse 14a, in an ASIC connected to the pixel electronics unit 12a for the pixel 1a, a corresponding counter result 24a is generated. As shown, the counting event 24a must not necessarily correspond in its temporal duration to the duration of the exceeding of the upper threshold value 20 by the voltage pulse 14a, but can be generated as a normalized on-off signal.

In the detector pixel 1b also, a counting event 24b is generated as a consequence of the exceeding of the upper threshold value 20 by the peak 16b of the voltage pulse 14b. Since, however, the voltage pulse 14b also has an underswing 26 as a consequence of the induced charge, this can be set with a corresponding selection of the lower threshold value 22 between the reference value 18 and the negative peak 28 of the underswing 26 such that a voltage pulse 14b of sufficient signal amplitude also leads in the correction signal 30 to a corresponding counting event 32. The counting events 24b in the second electrical signal and 32 in the correction signal 30 are herein temporally so close to one another that they are perceived in the time resolving capacity of the count rate—which is represented by the region shown—as simultaneous.

This is now the basis for a correction: for the subsequent generation of the images, only those counting events 24a are used for which in the context of the time resolution no corresponding counting event 32 is present in the correction signal 30 for the same pixel. It can thus be ensured that what is concerned is a unipolar voltage pulse of the type 14a and not a bipolar voltage pulse of the type 14b. Due to the pulse formation of the first electrical signal as a voltage signal from the current signals of the detector pixels 1a-1c which always converts unipolar current pulses into unipolar voltage pulses and therefore bipolar voltage pulses can only originate from bipolar current pulses, it can thus be concluded that the corresponding counting event 24a was in fact evoked by an X-ray photon and not by the influence of the charges which were originally generated by an X-ray photon in the adjacent pixel.

For the actual correction of the image data set generated on the basis of the second signal, by way of the correction signal 30, there are several possibilities. These are illustrated in the following figures.

Figure 4:
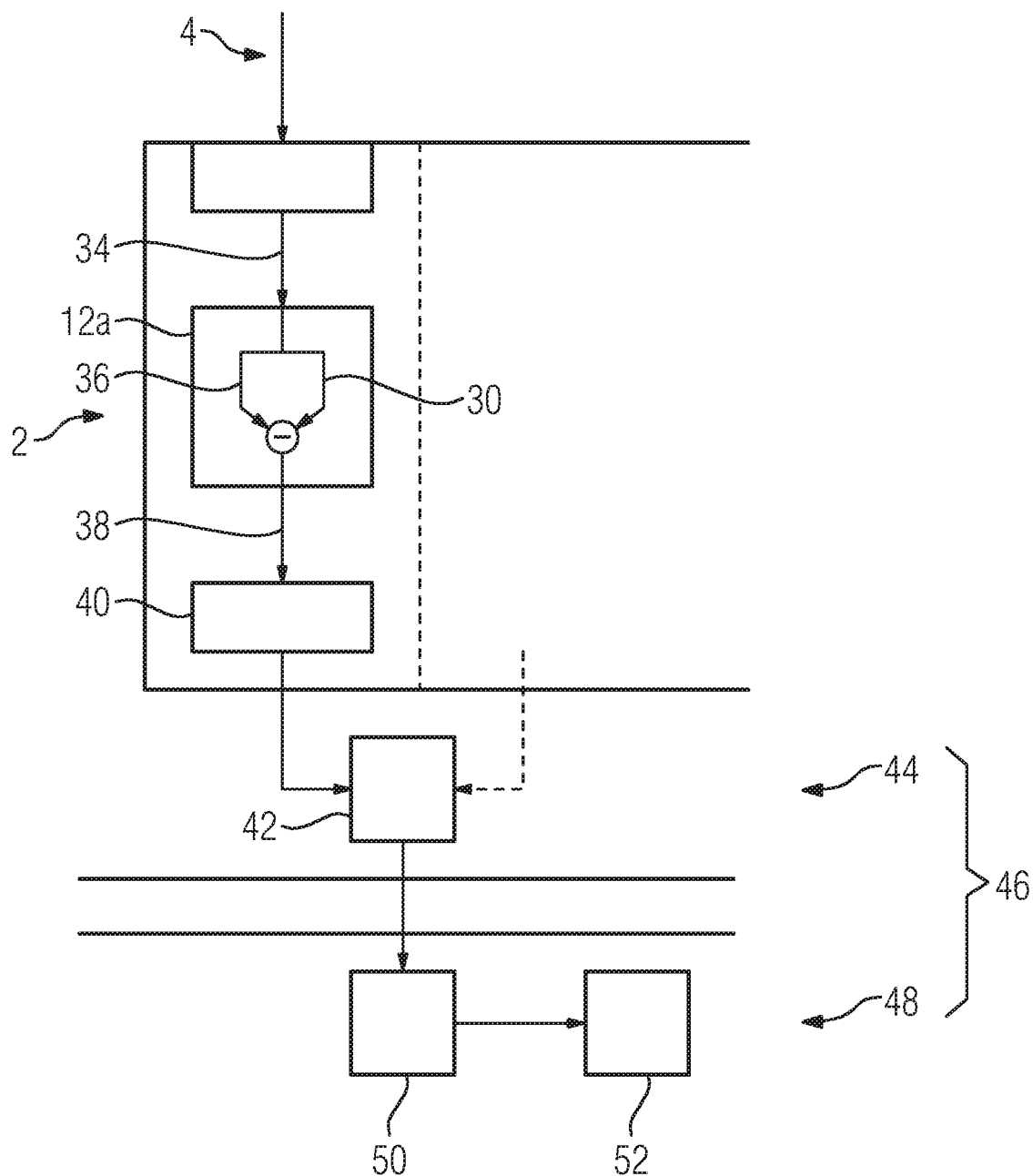
FIG. 4 is a CT system with an X-ray detector in which the correction according to FIG. 3 takes place in the pixel electronics unit.

FIG. 4 shows schematically a block circuit diagram of a quantum-counting X-ray detector 2 in which an incidence of the X-ray photon 4 initially leads to a signal contribution in a first electrical signal 34 which is converted in the pixel electronics unit 12a to a signal contribution in a second electrical signal 36. Still in the pixel electronics unit 12a, from the first electrical signal 34, the signal contributions for the correction signal 30 according to FIG. 3 are generated and the second electrical signal 36 is corrected locally in the pixel electronics unit 12a by the correction signal 30. This can take place, for example, in that the positive signal contributions of a bipolar current pulse in the first electrical signal is cleaned of the negative signal contributions of the current pulse.

The third electrical signal 38 resulting therefrom is amplified in an ASIC 40 and subsequently, the individual signal contributions of the third electrical signal 38 are passed on by the individual ASICs 40 to a central signal processing unit. From the central signal processing unit 42 which is also designated the "module back plane" and which is arranged on the rotating portion 44 of the CT 46, the correspondingly processed data are transferred to the fixed portion 48 of the CT 46 and an image data set 52 is generated there in an image processing unit 50.

Figure 5:
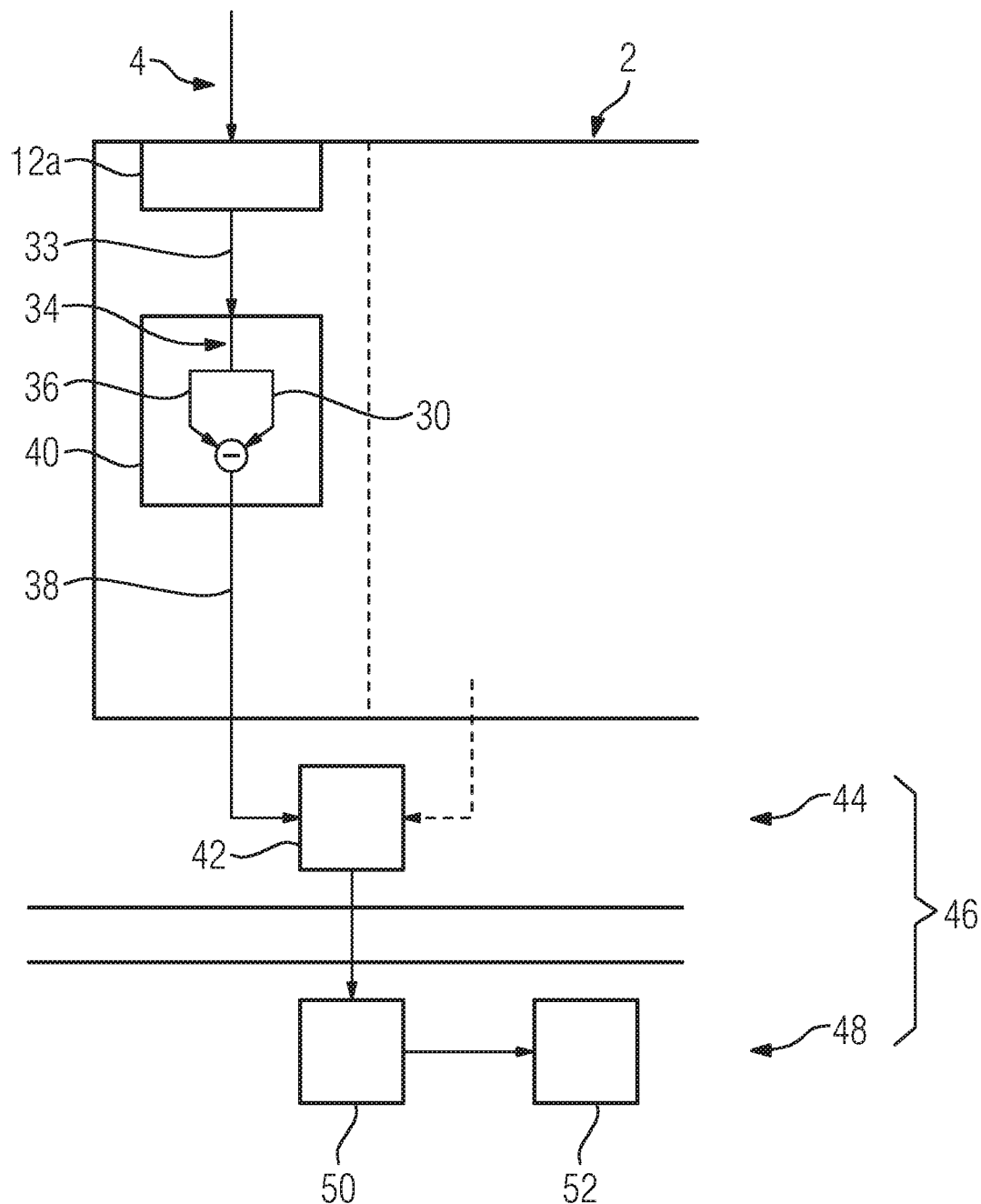
FIG. 5 is a CT system with an X-ray detector in which the correction according to FIG. 3 takes place in an ASIC connected downstream of the pixel electronics unit.

FIG. 5 shows a correction possibility which provides an alternative to that shown in FIG. 4. The X-ray photon 4 is herein incident upon the quantum-counting X-ray detector 2 from which a current pulse 33 is generated in the pixel electronics unit 12a. This is then converted in the ASIC 40 into the first electrical signal 34 from which the signal contributions of the second electrical signal 36 and of the correction signal 30 are generated. On the basis of the signal contributions of the second electrical signal 36 and of the correction signal 30, the actual correction takes place in the ASIC 40. The correspondingly generated third electrical signal 38 is output to the central signal processing unit 42 and from there is transferred to the fixed portion 48 of the CT 46 where the image data set 52 is generated in the image processing unit 50.

Figure 6:
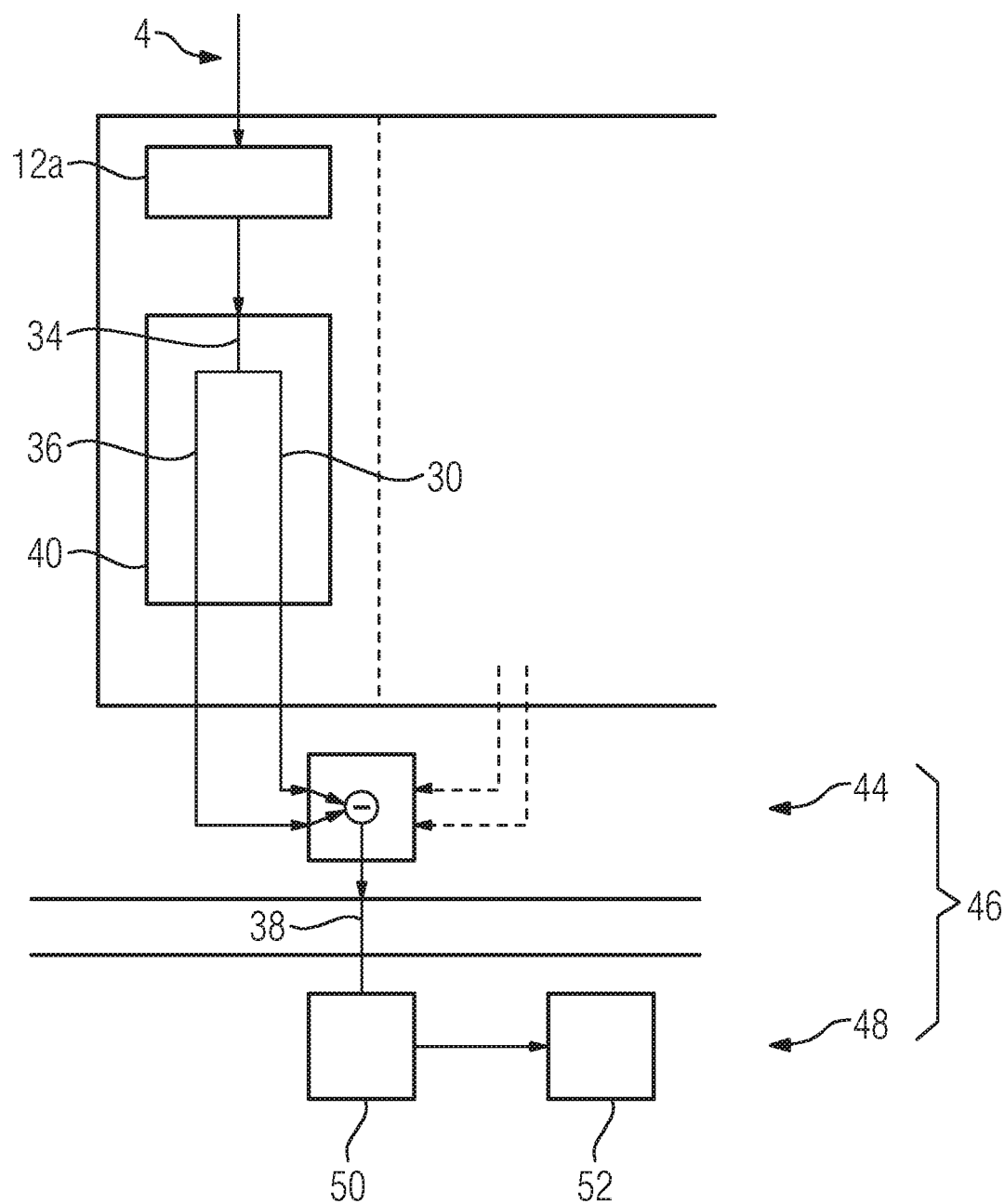
FIG. 6 is a CT system with an X-ray detector in which the correction according to FIG. 3 takes place in a central signal processing unit connected downstream of the ASICs.

A further alternative of the correction to that shown in FIGS. 4 and 5 is shown schematically in FIG. 6. In the circuit diagram shown there, the second electrical signal 36 of which the counting events and/or therefore signal contributions comprise the actual photon counts and possible induction-based phenomena, and the correction signal, the counting events of which exclusively comprise insolvency-based phenomena, are each passed on by the ASIC 40 to the central processing 42 where the actual correction takes place. The correspondingly generated third electrical signal 38 is then passed on from the central signal processing unit 42 on the rotating portion 44 of the CT 46 to the fixed portion 48 and from this the image data set 52 is generated in the image processing unit 50.

Figure 7:
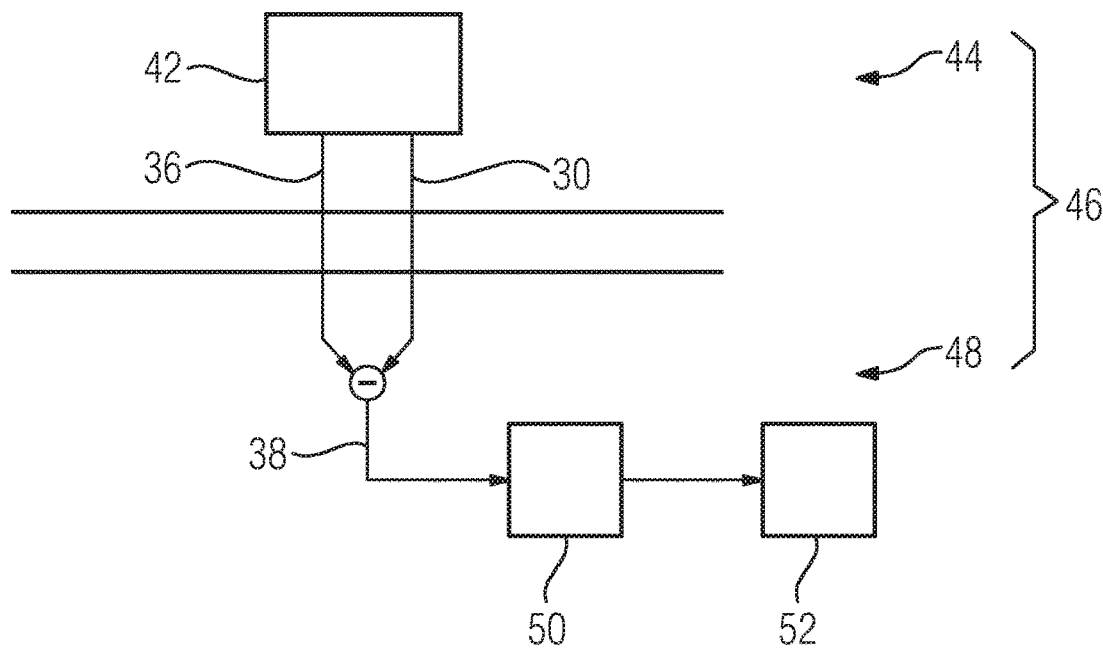
FIG. 7 is a CT system with an X-ray detector in which the correction according to FIG. 3 takes place after a data transmission on the fixed portion.
Figure 8:
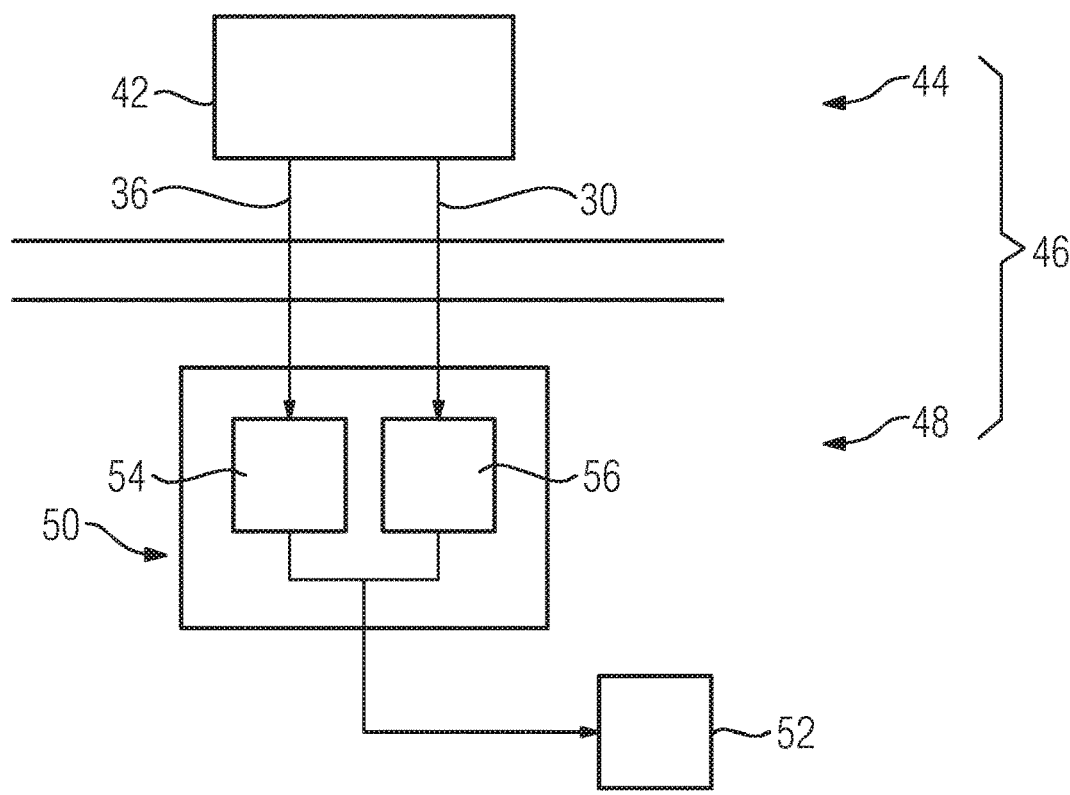
FIG. 8 is a CT system with an X-ray detector in which the correction according to FIG. 3 takes place by way of a correction image generated on the basis of the correction signal.

The correction of the counting events, however, can take place on the fixed portion 48 of the CT 46. This is illustrated in FIGS. 7 and 8. In the example embodiment of FIG. 7, the second electrical signal 36, that is, the pixel-wise counting events above the upper threshold value, and the correction signal 30, that is, the pixel-wise counting events below the lower threshold value are each separately transferred to the central signal processing unit 42. The signals then comprise the counting events of all the detector pixels. From the central signal processing unit 42 both the second electrical signal and also the correction signal, possibly following a corresponding post-processing, are transferred, still separately, from the rotation portion 44 to the fixed portion 48 of the CT 46.

In the example embodiment of FIG. 7, the correction of the second electrical signal 36 takes place by way of the correction signal 30 and the corresponding generation of the third electrical signal 38 takes place before the image processing unit. The image processing unit 50 then generates the image data set 52 from the corrected, that is the third, electrical signal 38.

In the example embodiment of FIG. 8, both the second electrical signal 36 and also the correction signal 30 are each transferred to the image processing unit 50. From the second electrical signal, a data set of preliminary image data 54 is now generated and from the correction signal 30, a correction image data set 56 is generated. The final image data set 52 is then generated through the correction of the preliminary image data set 54 with the correction image data set 56.

Figure 9:
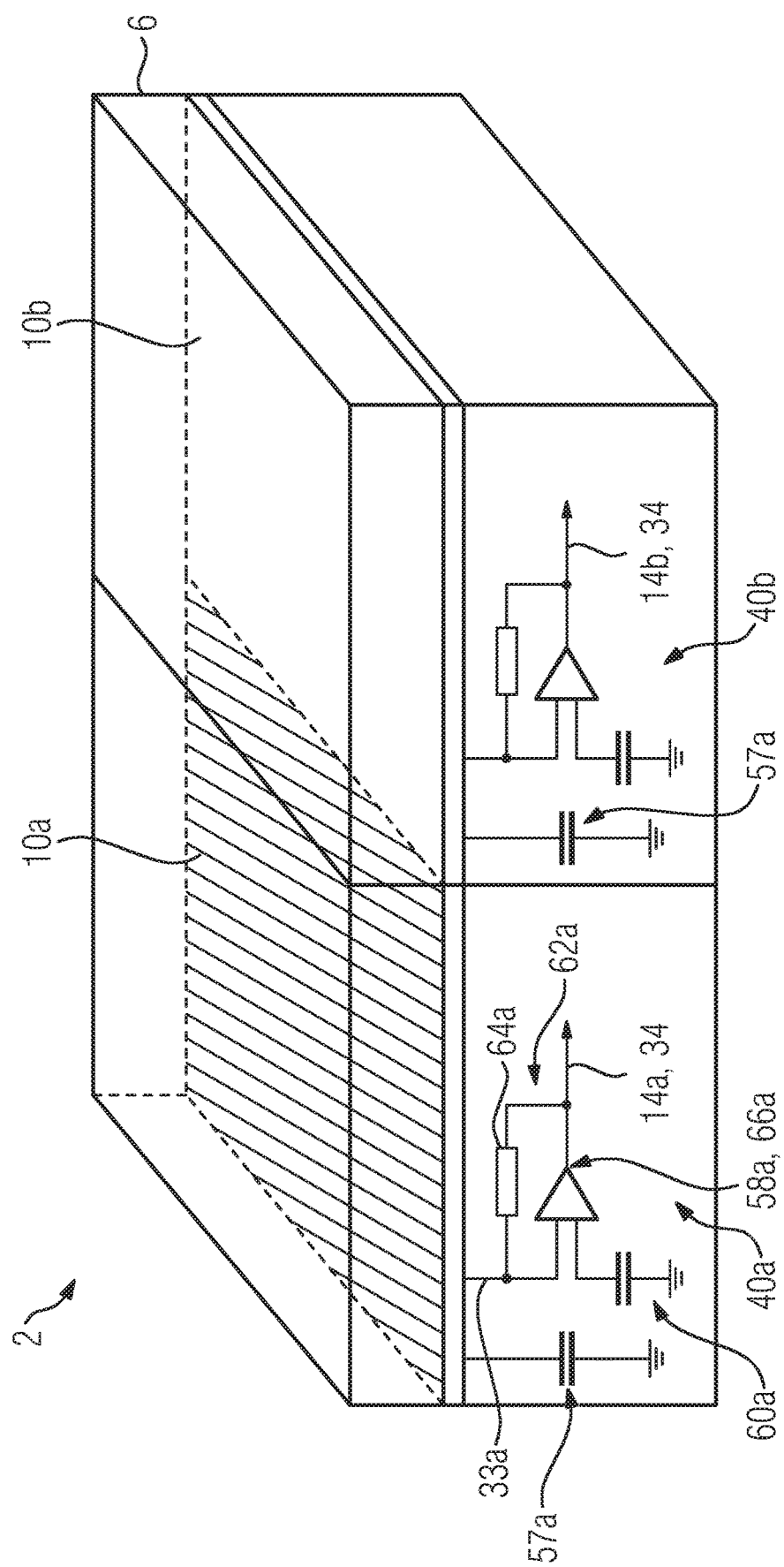
FIG. 9 is an oblique view of an X-ray detector for generating the voltage pulses according to FIGS. 2 and 3.

Shown schematically in FIG. 9 is an X-ray detector 2. The X-ray detector 2 comprises a semiconductor crystal 6 as the converting detector material. The electrons generated by an incident X-ray photon in the semiconductor crystal 6 are now each collected spatially resolved by an electrode arrangement which comprises the anode pixels 10a, 10b. For this purpose, a bias voltage 57a, 57b is applied to each of the anode pixels 10a, 10b.

The anode pixels 10a, 10b are each connected to an ASIC 40a, 40b. In the ASIC 40a, a current pulse 33a generated by the anode pixel 10a is fed to an amplifier stage 58a which in the present case is configured as a transimpedance amplifier. The amplifier stage 58a herein has a supply voltage 60a and a feedback member 62a with a resistance 64a, by which the resultant first electrical signal 34 is fed back into the current pulses 33a generated by the anode pixel 10a. The amplifier stage 58a thus functions as a current-voltage converter 66a which generates a corresponding voltage pulse 14a from the current pulse 33a in a spatially resolved manner in the first electrical signal 34. The further processing of the first electrical signal 34 then takes place in the manner described.

Although the invention has been illustrated and described in detail with the preferred example embodiment, the invention is not restricted by this example embodiment. Other variations can be derived therefrom by a person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for correcting a spatially resolved photon scan of an X-ray detector, comprising:
   generating in the X-ray detector, from an incident X-ray photon, a signal contribution of a first electrical signal in a spatially resolved manner, a reference value for the first electrical signal being defined by an absence of X-ray photons;
   selecting, for the first electrical signal, an upper threshold value above the reference value and selecting a lower threshold value below the reference value;
   first comparing the first electrical signal in a spatially resolved manner with the upper threshold value;
   generating, upon the first comparing indicating that the upper threshold value is exceeded, a signal contribution of a second electrical signal, spatially resolved;
   second comparing the first electrical signal, in a spatially resolved manner with the lower threshold value;
   generating, upon the second comparing indicating that the lower threshold value is undershot, a signal contribution of a correction signal;
   correcting the second electrical signal based upon the correction signal; and
   generating, based upon the second electrical signal corrected, an image data set.

2. The method of claim 1, wherein the signal contribution of the first electrical signal is generated in a quantum-counting manner.

3. The method of claim 2, wherein a ratio of an amount of the lower threshold value and an amount of the upper threshold value, each relative to the reference value, is selected to be between 0.3 and 3.

4. The method of claim 3, wherein the lower threshold value is selected to be in an interval from 5 keV to 15 keV below the reference value.

5. The method of claim 2, wherein the lower threshold value is selected to be in an interval from 5 keV to 15 keV below the reference value.

6. The method of claim 2, wherein the second electrical signal is locally corrected by the correction signal in a pixel electronics unit of the X-ray detector, and based upon the second electrical signal locally corrected, a third electrical signal is generated, and wherein the image data set is generated based upon the third electrical signal.

7. The method of claim 2, wherein the second electrical signal and the correction signal are each passed on by a pixel electronics unit (of the X-ray detector to an application-specific integrated circuit, wherein the second electrical signal is locally corrected in the application-specific integrated circuit by the correction signal, and based upon the second electrical signal locally corrected, a third electrical signal is generated, and wherein the image data set is generated based upon the third electrical signal.

8. The method of claim 2, wherein the second electrical signal and the correction signal are each transferred by an application-specific integrated circuit to a central signal processing unit, wherein the second electrical signal is corrected in the central signal processing unit, and based upon the second electrical signal corrected, a third electrical signal is generated, and wherein the image data set is generated based upon the third electrical signal.

9. The method of claim 2, wherein the second electrical signal and the correction signal are each transferred by a central signal processing unit on a rotating part of a computed tomography system to a fixed part of the computed tomography system, wherein the second electrical signal is corrected on the fixed part of the computed tomography system, and based upon the second electrical signal corrected, a third electrical signal is generated and wherein the image data set is generated based upon the third electrical signal.

10. The method of claim 2, wherein the second electrical signal and the correction signal are each transferred to an image processing unit, wherein a data set of preliminary image data is generated from the second electrical signal, wherein a correction image data set is generated from the correction signal, and wherein the image data set is generated from the data set of preliminary image data and the correction image data set.

11. The method of claim 1, wherein a ratio of an amount of the lower threshold value and an amount of the upper threshold value, each relative to the reference value, is selected to be between 0.3 and 3.

12. The method of claim 1, wherein the lower threshold value is selected to be in an interval from 5 keV to 15 keV below the reference value.

13. The method of claim 1, wherein the second electrical signal is locally corrected by the correction signal in a pixel electronics unit of the X-ray detector, and based upon the second electrical signal locally corrected, a third electrical signal is generated, and wherein the image data set is generated based upon the third electrical signal.

14. The method of claim 1, wherein the second electrical signal and the correction signal are each passed on by a pixel electronics unit (of the X-ray detector to an application-specific integrated circuit, wherein the second electrical signal is locally corrected in the application-specific integrated circuit, and based upon the second electrical signal locally corrected, a third electrical signal is generated, and wherein the image data set is generated based upon the third electrical signal.

15. The method of claim 1, wherein the second electrical signal and the correction signal are each transferred by an application-specific integrated circuit to a central signal processing unit, wherein the second electrical signal is corrected in the central signal processing unit, and based upon the second electrical signal corrected, a third electrical signal is generated, and wherein the image data set is generated based upon the third electrical signal.

16. The method of claim 1, wherein the second electrical signal and the correction signal are each transferred by a central signal processing unit on a rotating part of a computed tomography system to a fixed part of the computed tomography system, wherein the second electrical signal is corrected on the fixed part of the computed tomography system, and based upon the second electrical signal corrected, a third electrical signal is generated and wherein the image data set is generated based upon the third electrical signal.

17. The method of claim 1, wherein the second electrical signal and the correction signal are each transferred to an image processing unit, wherein a data set of preliminary image data is generated from the second electrical signal, wherein a correction image data set is generated from the correction signal, and wherein the image data set is generated from the data set of preliminary image data and the correction image data set.

18. An X-ray detector for spatially resolved detection of X-ray photons, the X-ray detector comprising:
processing circuitry configured to:
generate, from an incident X-ray photon, a signal contribution in a first electrical signal in a spatially resolved manner, a reference value being defined by an absence of X-ray photons;
resolve, in relation to the reference value, positive signal contributions of the first electrical signal and negative signal contributions of the first electrical signal; and
provide the positive signal contributions resolved and the negative signal contributions resolved for further processing.

19. The X-ray detector of claim 18, further comprising:
a converting detector material to generate charge carriers from an incident X-ray photon;
a spatially resolving electrode arrangement; and
a plurality of current-voltage converters,
wherein the processing circuitry is further configured to
generate a spatially resolved signal contribution in the first electrical signal from the charge carriers generated through the incident X-ray photon, and spatially resolved via the spatially resolving electrode arrangement, to generate a current pulse, and
generate, based upon the current pulse converted via one of the plurality of current-voltage converters, a voltage pulse as a signal contribution in the first electrical signal.

20. The X-ray detector of claim 19, wherein the plurality of current-voltage converters are each configured, based upon a unipolar current pulse generated by an incident X-ray photon, to generate a unipolar voltage pulse and, based upon a bipolar current pulse, to generate a bipolar voltage pulse.

21. The X-ray detector of claim 20, wherein the plurality of current-voltage converters are each integrated into an application-specific integrated circuit, each including an amplifier stage.

22. An imaging medical device comprising:
an X-ray source for generating X-ray photons; and
the X-ray detector of claim 21.

23. An imaging medical device comprising:
an X-ray source for generating X-ray photons; and
the X-ray detector of claim 20.

24. An imaging medical device comprising:
an X-ray source for generating X-ray photons; and
the X-ray detector of claim 19.

25. An imaging medical device comprising:
an X-ray source for generating X-ray photons; and
the X-ray detector of claim 18.

26. The imaging medical device of claim 25, configured as a computed tomography system.

27. The imaging medical device of claim 25, configured as a C-arm device.

* * * * *